(12) United States Patent
Heim et al.

(10) Patent No.: US 9,474,567 B2
(45) Date of Patent: Oct. 25, 2016

(54) METHOD FOR COATING SURGICAL INSTRUMENTS

(71) Applicant: Team Medical, LLC, Boulder, CO (US)

(72) Inventors: Warren P. Heim, Boulder, CO (US); James Brassell, Boulder, CO (US)

(73) Assignee: Team Medical, LLC, Boulder, CO (US)

(*) Notice: Subject to any disclaimer, the term of this patent is extended or adjusted under 35 U.S.C. 154(b) by 63 days.

(21) Appl. No.: 14/516,782

(22) Filed: Oct. 17, 2014

(65) Prior Publication Data

US 2015/0141989 A1 May 21, 2015

Related U.S. Application Data

(63) Continuation of application No. 13/776,411, filed on Feb. 25, 2013, now abandoned, which is a continuation of application No. 13/398,543, filed on Feb. 16, 2012, now abandoned, which is a continuation of application (Continued)

(51) Int. Cl.
*A61B 18/14* (2006.01)
*C04B 24/42* (2006.01)
(Continued)

(52) U.S. Cl.
CPC .............. *A61B 18/14* (2013.01); *A61B 18/00* (2013.01); *A61L 31/088* (2013.01); *A61L 31/14* (2013.01);
(Continued)

(58) Field of Classification Search
CPC ........... A61B 18/14; C09D 5/16; C08F 2/48; C08K 5/24; C04B 12/04
USPC ............. 606/45, 41, 49; 106/15, 600, 287.1, 106/287.18, 287.19; 427/508; 524/261
See application file for complete search history.

(56) References Cited

U.S. PATENT DOCUMENTS 874,178 A 12/1907 De Forest
1,713,970 A 5/1929 Lowry et al.
(Continued)

FOREIGN PATENT DOCUMENTS

KR 10-2004-0007455 * 10/2005 .............. C09D 1/02
WO 94/28809 12/1994
(Continued)

OTHER PUBLICATIONS

Surfactant Definition, Hawley's Condensed Chemical Dictionary, 14th Edition, John Wiley & Sons, Inc., 2002.
(Continued)

*Primary Examiner* — Dah-Wei D Yuan
*Assistant Examiner* — Andrew Bowman
(74) *Attorney, Agent, or Firm* — Marsh Fischmann & Breyfogle LLP

(57) ABSTRACT

A coating and devices using the coating are provided. The coating is applied in liquid form and dried or otherwise cured to form a durable adherent coating resistant to high temperatures and having optional hydrophobic properties. The coating formulation contains an aqueous formulation of silica, one or more fillers, and sufficient base, (e.g., potassium hydroxide), to have a pH exceeding about 10.5 during at least part of the formulation process. The formulation may contain a compound(s) that affects surface free energy, energy to make the cured coating hydrophobic. Such compounds include silanes containing halogens (e.g., fluorine or chlorine) and in particular silanes containing one or more hydrolyzable groups attached to at least one silicon atom and a group containing one or more halogens (e.g., chlorine or fluorine). A medical instrument (e.g., electrosurgical instrument) may be at least partially covered by a coating using the formulation.

18 Claims, 3 Drawing Sheets

Related U.S. Application Data

No. 12/768,962, filed on Apr. 28, 2010, now abandoned, which is a continuation of application No. 11/627,340, filed on Jan. 25, 2007, now abandoned.

(60) Provisional application No. 60/762,375, filed on Jan. 25, 2006.

(51) Int. Cl.

| | | |
|---|---|---|
| *C04B 28/26* | (2006.01) | |
| *A61B 18/00* | (2006.01) | |
| *C09D 1/00* | (2006.01) | |
| *H01B 3/44* | (2006.01) | |
| *A61L 31/08* | (2006.01) | |
| *A61L 31/14* | (2006.01) | |
| *B05D 1/36* | (2006.01) | |
| *B05D 3/00* | (2006.01) | |
| *B05D 5/00* | (2006.01) | |
| *C04B 111/00* | (2006.01) | |
| *A61B 17/00* | (2006.01) | |

(52) U.S. Cl.
CPC ............... *B05D 1/36* (2013.01); *B05D 3/007* (2013.01); *B05D 5/00* (2013.01); *C04B 24/42* (2013.01); *C04B 28/26* (2013.01); *C09D 1/00* (2013.01); *H01B 3/445* (2013.01); *A61B 2017/00526* (2013.01); *A61L 2420/02* (2013.01); *A61L 2420/06* (2013.01); *A61L 2420/08* (2013.01); *C04B 2111/00482* (2013.01); *C04B 2111/00525* (2013.01); *C04B 2111/00836* (2013.01); *Y02W 30/94* (2015.05); *Y10T 428/259* (2015.01)

(56) References Cited

U.S. PATENT DOCUMENTS

| | | |
|---|---|---|
| 1,814,791 A | 7/1931 | Ende |
| 3,130,061 A | 4/1964 | McMahon et al. |
| 3,615,781 A | 10/1971 | Schneider et al. |
| 3,721,574 A | 3/1973 | Schneider et al. |
| 3,799,168 A | 3/1974 | Peters |
| 3,854,960 A * | 12/1974 | Plum .................. C09D 5/1631 106/18.31 |
| 3,855,172 A | 12/1974 | Iler et al. |
| 3,900,823 A | 8/1975 | Sokal et al. |
| 3,919,656 A | 11/1975 | Sokal et al. |
| 3,987,795 A | 10/1976 | Morrison |
| 4,043,342 A | 8/1977 | Morrison, Jr. |
| 4,074,718 A | 2/1978 | Morrison, Jr. |
| 4,087,878 A | 5/1978 | Grieshaber et al. |
| 4,092,986 A | 6/1978 | Schneiderman |
| 4,114,623 A | 9/1978 | Meinke et al. |
| 4,161,950 A | 7/1979 | Doss et al. |
| 4,184,197 A | 1/1980 | Cuk et al. |
| 4,186,437 A | 1/1980 | Cuk |
| 4,202,337 A | 5/1980 | Hren et al. |
| 4,228,800 A | 10/1980 | Degler, Jr. et al. |
| 4,248,231 A | 2/1981 | Herczog et al. |
| 4,257,087 A | 3/1981 | Cuk et al. |
| 4,274,133 A | 6/1981 | Cuk et al. |
| 4,307,720 A | 12/1981 | Weber, Jr. |
| 4,314,559 A | 2/1982 | Allen |
| 4,331,149 A | 5/1982 | Gonser |
| 4,333,467 A | 6/1982 | Domicone |
| 4,449,926 A | 5/1984 | Weiss |
| 4,481,057 A | 11/1984 | Beard |
| 4,492,231 A | 1/1985 | Auth |
| 4,534,347 A | 8/1985 | Taylor |
| 4,545,375 A | 10/1985 | Cline |
| 4,555,545 A | 11/1985 | Kimura et al. |
| 4,565,200 A | 1/1986 | Cosman |
| 4,589,411 A | 5/1986 | Friedman |
| 4,617,927 A | 10/1986 | Manes |
| 4,622,966 A | 11/1986 | Beard |
| 4,657,016 A | 4/1987 | Garito et al. |
| 4,658,819 A | 4/1987 | Harris et al. |
| 4,676,242 A | 6/1987 | Doi |
| 4,704,760 A | 11/1987 | Grieshaber |
| 4,752,983 A | 6/1988 | Grieshaber |
| 4,785,807 A | 11/1988 | Blanch |
| 4,793,346 A | 12/1988 | Mindich |
| 4,823,791 A | 4/1989 | D'Amelio et al. |
| 4,848,337 A | 7/1989 | Shaw et al. |
| 4,852,200 A | 8/1989 | Phillips et al. |
| 4,898,618 A | 2/1990 | Holcombe, Jr. et al. |
| 4,925,516 A | 5/1990 | Phillips et al. |
| 4,927,420 A | 5/1990 | Newkirk et al. |
| 4,931,047 A | 6/1990 | Broadwin et al. |
| 4,976,711 A | 12/1990 | Parins et al. |
| 5,015,227 A | 5/1991 | Broadwin et al. |
| 5,016,401 A | 5/1991 | Mangus |
| 5,030,218 A | 7/1991 | Alexander |
| 5,055,137 A | 10/1991 | Holcombe, Jr. et al. |
| 5,078,078 A | 1/1992 | Cuk |
| 5,080,660 A | 1/1992 | Buelna |
| 5,085,657 A | 2/1992 | Ben-Simhon |
| 5,088,997 A | 2/1992 | Delahuerga et al. |
| 5,160,334 A | 11/1992 | Billings et al. |
| 5,167,659 A | 12/1992 | Ohtomo et al. |
| 5,197,963 A | 3/1993 | Parins |
| 5,219,348 A | 6/1993 | Buess et al. |
| 5,267,994 A | 12/1993 | Gentelia et al. |
| 5,267,997 A | 12/1993 | Farin et al. |
| 5,308,311 A | 5/1994 | Eggers et al. |
| 5,313,943 A | 5/1994 | Houser et al. |
| 5,318,562 A | 6/1994 | Levy et al. |
| 5,318,563 A | 6/1994 | Malis et al. |
| 5,322,503 A | 6/1994 | Desai |
| 5,370,645 A | 12/1994 | Klicek et al. |
| 5,380,320 A | 1/1995 | Morris |
| 5,382,247 A | 1/1995 | Cimino et al. |
| 5,416,387 A | 5/1995 | Cuk et al. |
| 5,437,662 A | 8/1995 | Nardella |
| 5,442,534 A | 8/1995 | Cuk et al. |
| 5,442,539 A | 8/1995 | Cuk et al. |
| 5,464,390 A | 11/1995 | Arnett et al. |
| 5,472,442 A | 12/1995 | Klicek |
| 5,472,443 A | 12/1995 | Cordis et al. |
| 5,496,312 A | 3/1996 | Klicek |
| 5,520,684 A | 5/1996 | Imran |
| 5,539,630 A | 7/1996 | Pietkiewicz et al. |
| 5,540,681 A | 7/1996 | Strul et al. |
| 5,545,161 A | 8/1996 | Imran |
| 5,549,604 A | 8/1996 | Sutcu et al. |
| 5,554,172 A | 9/1996 | Horner et al. |
| 5,556,396 A | 9/1996 | Cohen et al. |
| 5,570,276 A | 10/1996 | Cuk et al. |
| 5,630,426 A | 5/1997 | Eggers et al. |
| 5,633,578 A | 5/1997 | Eggers et al. |
| 5,643,256 A | 7/1997 | Urueta |
| 5,693,045 A | 12/1997 | Eggers |
| 5,693,060 A | 12/1997 | Speiser |
| 5,697,909 A | 12/1997 | Eggers et al. |
| 5,697,926 A | 12/1997 | Weaver |
| 5,702,387 A | 12/1997 | Arts et al. |
| 5,707,402 A | 1/1998 | Heim |
| 5,713,895 A | 2/1998 | Lontine et al. |
| 5,766,153 A | 6/1998 | Eggers et al. |
| 5,800,426 A | 9/1998 | Taki et al. |
| 5,817,093 A | 10/1998 | Williamson, IV et al. |
| 5,833,686 A | 11/1998 | Zhao |
| 5,836,943 A | 11/1998 | Miller |
| 5,891,095 A | 4/1999 | Eggers et al. |
| 5,957,922 A | 9/1999 | Imran |
| 5,998,525 A | 12/1999 | Wang et al. |
| 6,016,452 A | 1/2000 | Kasevich |
| 6,030,218 A | 2/2000 | Robinson |
| 6,030,381 A | 2/2000 | Jones et al. |
| 6,039,735 A | 3/2000 | Greep |

(56) References Cited

U.S. PATENT DOCUMENTS

| | | | |
|---|---|---|---|
| 6,059,783 A | 5/2000 | Kirwan, Jr. | |
| 6,066,137 A | 5/2000 | Greep | |
| 6,074,387 A | 6/2000 | Heim et al. | |
| 6,106,519 A | 8/2000 | Long et al. | |
| 6,126,656 A | 10/2000 | Billings | |
| 6,132,427 A | 10/2000 | Jones et al. | |
| 6,228,081 B1 | 5/2001 | Goble | |
| 6,238,387 B1 | 5/2001 | Miller | |
| 6,241,723 B1 | 6/2001 | Heim et al. | |
| 6,287,305 B1 | 9/2001 | Heim et al. | |
| 6,413,255 B1 | 7/2002 | Stern | |
| 6,533,781 B2 | 3/2003 | Heim et al. | |
| 6,685,704 B2* | 2/2004 | Greep | A61B 18/14 606/41 |
| 6,692,489 B1 | 2/2004 | Heim et al. | |
| 6,758,846 B2 | 7/2004 | Goble et al. | |
| 6,793,728 B1* | 9/2004 | Davies | C09D 1/02 106/287.1 |
| 7,377,919 B2 | 5/2008 | Heim et al. | |
| 2001/0031964 A1* | 10/2001 | Gentelia | A61B 18/1402 606/45 |
| 2002/0193460 A1 | 12/2002 | Kovar et al. | |
| 2003/0109864 A1 | 6/2003 | Greep et al. | |
| 2005/0239933 A1* | 10/2005 | Lee | C09D 165/00 524/261 |
| 2006/0025757 A1 | 2/2006 | Heim | |
| 2006/0286305 A1* | 12/2006 | Thies | B82Y 30/00 427/508 |

FOREIGN PATENT DOCUMENTS

| | | |
|---|---|---|
| WO | 96/34571 | 11/1996 |
| WO | 97/11649 | 4/1997 |
| WO | 98/47436 | 10/1998 |

OTHER PUBLICATIONS

Surface-Active Agent Definition, Hawley's Condensed Chemical Dictionary, 14th Edition, John Wiley & Sons, Inc., 2002.
Schmidt, H., Chemistry of Material Preparation by the Sol-Gel Process, Journal of Non-Crystalline Solids 100, Elsevier Science Publishers B.V., 1988, pp. 51-64.
Handbook of Adhesives and Surface Preparation, S. Ebnesajjad, p. 336 (2011).
KR1020050079288 (2005).
English Machine Translation of KR1020050079288 (2005).
H Schmidt JI NonCrystalline Solids vol. 100 pp. 51-64 (1988).

* cited by examiner

METHOD FOR COATING SURGICAL INSTRUMENTS

RELATED APPLICATIONS

This is a continuation of U.S. patent application Ser. No. 13/776,411, filed Feb. 25, 2013, entitled "COATING SUITABLE FOR SURGICAL INSTRUMENTS," which application was a continuation of U.S. patent application Ser. No. 13/398,543, filed Feb. 16, 2012, entitled "COATING SUITABLE FOR SURGICAL INSTRUMENTS," which application was a continuation of U.S. patent application Ser. No. 12/768,962 filed Apr. 28, 2010, entitled "COATING SUITABLE FOR SURGICAL INSTRUMENTS," which application was a continuation of U.S. patent application Ser. No. 11/627,340 filed Jan. 25, 2007, entitled "COATING SUITABLE FOR SURGICAL INSTRUMENTS," which application claimed priority to U.S. Provisional Patent Application No. 60/762,375 filed Jan. 25, 2006, entitled "COATING FOR SURGICAL INSTRUMENTS AND RELATED METHODS AND APPARATUS," each of which applications are incorporated herein by reference in their entirety.

FIELD OF THE INVENTION

The present invention relates to materials' coatings and using coatings to protect and affect the surface properties of products or apparatus at least partially covered with such coatings, such as instruments used during surgical procedures. The invention may be used in applications where coatings are useful and more particularly for applications benefitting from containing one or components containing materials benefitting from protecting the component from the use environment or the use environment from the component. Examples of such protection are protecting components from high temperatures, liquids or vapors, such as moisture or steam, or protecting materials in the use environment from high temperature components. The invention is advantageous where an adherent coating able to withstand high temperatures, such as a coating being adherent to metals, protects components from the use environment or protects elements of the use environment from components. An example of such use is on instruments that apply electrosurgical power to a tissue site to achieve a predetermined surgical effect. Another example of such use is coating engine exhaust components such as mufflers. Another example of such use is coating doors to improve thermal or oxidative resistance, such as fire doors. Aspects of the present invention include a composition for coating formulation, a method for preparing the composition, and a method for forming a coating using the composition.

BACKGROUND OF THE INVENTION

Electrical energy is widely employed during surgical procedures in which electrosurgical techniques are employed to provide localized high flux energy to tissue during open, laparoscopic, and arthroscopic applications to provide clinical benefits, such as hemostasis, relative to surgical approaches that use mechanical cutting such as scalpels. Electrosurgical techniques typically entail the use of a hand-held instrument, or pencil, that transfers alternating current electrical power operating at radio frequency (RF) to tissue at the surgical site. The time-varying RF electrical power yields a predetermined electrosurgical effect, such as tissue cutting or coagulation.

The process of applying RF electrical power causes high temperatures to occur in the tissue and on at least part of the surgical instrument. The result of these high temperatures is the formation of tissue fragments and other substances that often accumulate and form deposits on surgical instruments. These deposits are called eschar. Eschar frequently accumulates in such amounts that it interferes with surgical procedures.

In attempts to alleviate the formation of eschar or make instruments from which eschar may be more easily removed than from metal surfaces, instruments with surface coatings, such as coated blades, have been used or described. For example, such coatings are made from materials to which eschar accumulations stick less tightly than they stick to the metals from which electrosurgical instruments are made. The coatings are typically made from one or more polydiorganosiloxane or polytetrafluorethylene (PTFE) compounds. These compounds suffer from not having high temperature durability. Materials capable of withstanding high temperatures, such as ceramics, do not confer adequate non-stick properties when used as coatings. In this regard, the present inventors have recognized that the need exists for a high temperature coating that has non-stick properties.

Relatedly, the metal conductors in electrosurgical instruments that convey energy to tissue get hot during use. When contacting tissue the hot surfaces damage tissue. Therefore, protecting tissue in the use environment from the hot instrument surfaces can reduce tissue damage. Typical coatings cannot withstand the high temperatures in regions directly adjacent to where RF electrical power transfers to tissue. In this regard, the present inventors have also recognized that the need exists for a high temperature coating with insulating properties.

In general, the present inventors believe that the need exists for a coating that can protect component materials from the use environment and the use environment from components.

SUMMARY OF THE INVENTION

Accordingly, an objective of the present invention is to provide a coating formulation, method for preparing the coating formulation, and method for applying the coating formulation to one or more components in an apparatus that needs protection from the use environment or that needs to have the use environment protected from the apparatus.

An objective of the present invention is to provide a coating formulation, method for preparing the coating formulation, and method for applying the coating formulation to one or more components of devices used in surgical environments.

An objective of the present invention is to provide a coating formulation, method for preparing the coating formulation, and method for applying the coating formulation to one or more components of devices used in surgical environments that results in a durable high temperature nonstick coating.

Another objective of the present invention is to provide a coating formulation, method for preparing the coating formulation, and method for applying the coating formulation to a surgical instrument powered by electrosurgical energy that results in reduced eschar accumulation.

In addressing these objectives, the present inventors have recognized that a novel coating formulation containing silica (e.g., colloidal and/or amorphous silica), inorganic fillers, and a strong base such that the pH of the formulation exceeds 10.5 during at least part of the preparation process produces a durable adherent high temperature coating to which a treatment such as a non-stick outer coating may be applied. In this regard, the use of a strong base advantageously serves to at least partially dissolve the silica.

In one aspect, the present inventors have further recognized that a novel coating containing silica (e.g., colloidal and/or amorphous silica), inorganic fillers, and a strong base such that the pH of the formulation exceeds 10.5 during at least part of the preparation process, and which additional constituents such as alkoxy silanes may be added, produces a coating that is inherently non-stick, adherent, durable, and capable of withstanding high temperatures. The present inventors have further recognized that such coatings have non-stick properties when the formulation contains one or more halogen-containing alkylalkoxysilanes, e.g., those containing halogens such as fluorine or chlorine. In the latter regard, and by way of example, fluoroalkylalkoxysilanes or chloroalkylalkoxysilanes may be employed.

The present inventors have yet further recognized that such use of alkylalkoxysilanes possessing hydrolyzable inorganic alkylsilyl groups including methoxysilyl or ethoxysilyl groups produces durable high temperature coatings. The present inventors have yet further recognized that using alkylalkoxysilanes possessing hydrolyzable inorganic alkylsilyl groups including methoxysilyl or ethoxysilyl groups and one or more straight or branched halogenalkyl chains, such as chloroalkyl or fluoroalkyl chains, produces durable high temperature coatings with excellent hydrophobic and oleophobic (non-stick) properties.

The present inventors have yet further recognized that a coating containing silica (e.g., colloidal and/or amorphous silica), inorganic fillers, and a strong base such that the pH of the formulation exceeds 10.5 during at least part of the formulation process to which one or more substance containing one or more fluorinated carbon chains, such as PTFE emulsions or at least partially hydrolyzed fluorinated silanes or at least partially cross-linked hydrolyzed silanes, form a coating that is inherently non-stick, adherent, durable, and capable of withstanding high temperatures.

In another aspect, the present inventors have further recognized that adding materials such as water, surfactants, and solids such as fumed silica alter the viscosity and surface tension of the formulation to allow it to flow or otherwise cover surfaces producing coatings having different thicknesses or surface finishes and making coatings suitable for various application methods such as dipping or spraying.

In further addressing the objectives of the present invention the inventors have recognized that the coating formulation of the present invention may be applied to organic and inorganic materials, such as cloth, glass, plastic, and metal materials and produce durable adherent coatings. Such coating may be restricted to the surface or may penetrate into interstitial pores, cracks, crevices, or other voids that exist.

In further addressing the objectives of the present invention the inventors have recognized that the coating formulation of the present invention may be applied to electrically conductive metal surfaces and produce durable adherent coatings suitable for use on medical instruments including instruments suitable for use with electrosurgery. The present inventors have further recognized that the coating formulation of the present invention may be applied to stainless steel and materials having thermal conductivities greater than stainless steel, such as molybdenum, and produce durable adherent coatings suitable for medical instruments including instruments suitable for use with electrosurgery. The present inventors have further recognized that surgical instruments comprised at least in part with metals having coatings based on the formulation of the present invention are most suitable for use in electrosurgical applications when at least one part of the metal surface is left uncoated or sufficiently thinly coated so that an energy transfer path exists with sufficiently low impedance, less than approximately 5,000 ohms, that electrosurgical energy can adequately transfer from the surgical instrument to the tissue where a predetermined surgical effect is desired to occur.

In still further addressing the objectives of the present invention the inventors have recognized that the coating formulation of the present invention may be applied by dipping, spraying, painting, printing, pad printing, or other means capable of transferring a liquid substance to a substrate such as one made from metal or a surgical instrument. In still further addressing the objectives for the present invention the inventors have recognized that the coating formulation of the present invention may be applied in multiple coats to build up a final coat. The present inventors have further recognized that such multiple coats may be applied prior to applying energy to any already applied coat, such application of energy being applied to cure the coating material.

In still further addressing the objectives of the present invention the inventors have recognized that the coating formulation of the present invention may be cured by applying energy, such as thermal energy transferred by conduction from air or radiation from one or more surfaces, to enhance the properties of the coating, such as its durability, resistance to moisture, adherence, and non-stick properties.

In short, the present inventors have recognized that a durable coating is needed to improve the performance of apparatus, such as to prevent or reduce the formation or accumulation of the deposits that form on material surfaces such as the surfaces of surgical instruments powered by electrosurgical energy. The present invention comprises a coating formulation that includes colloidal silica, a strong base, one or more fillers, and optionally formulated with one or more substances that produce non-stick properties to the coating. Such substance that produce non-stick properties include alkoxy silanes, including alkoxy silanes having one or more chains containing at least some halogens such as chlorine or fluorine. The present invention further includes applying such coating formulations to surfaces to produce a coating on materials, including materials with organic or inorganic surfaces, including plastic, glass, and metallic surfaces, that is adherent, resistant to high temperatures, and non-stick. The present invention further comprises such metallic surfaces when they are at least part of a medical instrument, such as an electrosurgical instrument.

DETAILED DESCRIPTION

Figure 1:
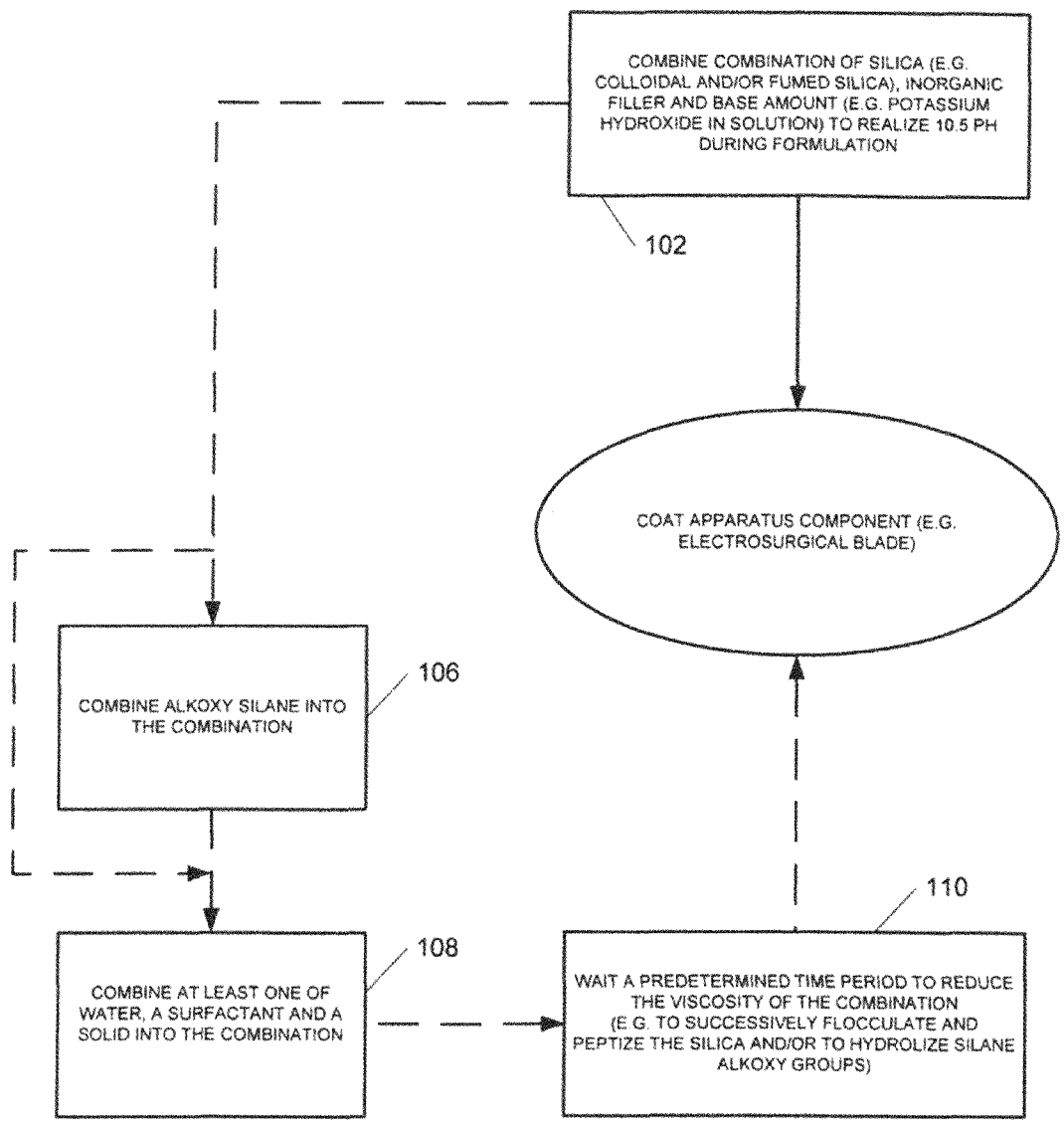
FIG. 1 illustrates one embodiment of a method of preparing inventive coating formulations in accordance with the present invention.

The present invention is for coating formulations capable of withstanding high temperatures and adherent to metal surfaces and that may be formulated to have a surface free energy that makes the surface substantially non-stick, meaning that the surface is substantially hydrophobic or oleophobic, or both. Such coating formulations have applicability when used to form a surface coat on surgical instruments receiving electrosurgical energy and contacting tissue to achieve a predetermined surgical effect. The present invention further includes applying the subject coating formulations and optionally enhancing the coating's properties by applying energy, such as thermal energy. The coating formulation comprises a silicate solution, such as a colloidal silicate solution, one or more fillers, and a strong base and optionally includes one or more materials that reduce the surface free energy to enhance the non-stick properties of the surface.

In one approach, a colloidal silicate solution may contain at least 10 weight percent silica. In another embodiment the colloidal silicate solution may contain about 50 weight percent silica. Representative examples of colloidal silicate solutions are alkali metal silicates, including those of lithium polysilicate, sodium silicate, and potassium silicate, and colloidal silica. The colloidal silicate solution may be colloidal silica with about 50 weight percent silica. The colloidal silica average particle size may be between about 5 nm and 100 nm and it may be between about 30 and 80 nm and it may be between about 40 and 80 nm. Example colloidal silica products are Megasol S50 (WesBond Corporation) and LEVASIL® 50/50% (H. C. Starck GmbH).

The coating formulation includes a strong base in a concentration that causes the pH of the formulation to exceed 10.5 at least at some point during the formulation process. The strong base functions to at least partially dissolve the silica. For example, the strong base may be added in sufficient amount to cause at least the initial pH to exceed 12 and the strong base may be added to exceed 12.5. The strong base used may be potassium hydroxide (KOH). The KOH may be added as a KOH solution consisting of KOH and water and the concentration of the solution may be approximately 50 weight percent KOH, or between approximately 20 percent and 80 percent.

The filler material may comprise various metal/non-metal combinations, including, for example, compositions that comprise the following: aluminum oxides (e.g., alumina and $Al_2O_3$), zirconium oxides (e.g., $Zr_2O_3$), zirconium nitrides (e.g., ZrN), zirconium carbides (e.g., ZrC), boron carbides (e.g., $B_4C$), silicon oxides (e.g., $SiO_2$), mica, magnesium-zirconium oxides (e.g., $(Mg—Zr)O_3$), zirconium-silicon oxides (e.g., $(Zr—Si)O_2$), titanium oxides (e.g., $TiO_2$) tantalum oxides (e.g., $Ta_2O_5$), tantalum nitrides (e.g., TaN), tantalum carbides (e.g., TaC), silicon nitrides (e.g., $Si_3N_4$), silicon carbides (e.g., SiC), tungsten carbides (e.g., WC) titanium nitrides (e.g., TiN), titanium carbides (e.g., TiC), nibobium nitrides (e.g., NbN), niobium carbides (e.g., NbC), vanadium nitrides (e.g., VN), vanadium carbides (e.g., VC), and hydroxyapatite (e.g., substances containing compounds such as $3Ca_3(PO_4)_2Ca(OH)_2Ca10(PO_4)_6(OH)_2Ca5(OH)(PO_4)_3$, and $Ca_{10}H_2O_{26}P_6$).

Filler materials may be of any shape including, for example, shapes that approximate in whole or in part or are substantially fibers, plates, spheres, rods, coils, or polyhedrons such as cubes or other shapes that may be approximated by a collection of polygons. Combinations of filler materials having more than one shape may be used. For example, fillers comprising one or more materials having fiber shapes and plate-like shapes may be used.

The filler may have one or more constituents comprising at least in part one or more inorganic fibers or inorganic powders such as those derived from clays with such fillers including those that contain silicon oxide, aluminum oxides, magnesium oxides, titanium oxides, chrome oxides, calcium oxides, or zirconium oxides. The filler materials may contain one or more materials that have at least 30 percent by weight $Al_2O_3$ or $SiO_2$ either alone or combined with other elements, such as occurs in kaolin, talc, or montmorillonite. Clays used may include substances that are members of the smectite group of phyllosilicate minerals. Representative examples of clay minerals include bentonite, talc, kaolin (kaolinite), mica, clay, sericite, hectorite, montmorillonite and smectite. In the present invention, at least one of kaolin, talc, and montmorillonite may be used. These clay minerals can be used singly or in combination.

The filler may have one or more constituents that are at least in part fibers that contain in part or wholly alumina or silica or calcium silicate, such as Wollastonite, alumina fiber, silica fiber or fibers containing a combination of alumina and silica.

At least one dimension, such as diameter, length, width, or particle size, of at least one of the filler materials may have a mean value of less than about 200 micrometers. The materials may have one or more material with one or more dimensions with a mean value of less than about 50 micrometers. The materials may have one or more dimensions with one or more mean values less than about 10 microns. The materials may have one or more dimensions with one or more mean values less than about 5 microns, such as both the diameter and thickness being less than about 5 microns.

When montmorillonite is used as a filler it may be a form that is untreated or it may be a form that has been treated with a surface modifying process, such as a treatment to enhance its dispersion. When used, montmorillonite may be a form that has been onium ion treated. An example onium ion treated montmorillonite is Nanomer® I.44P (Nanocor, Inc.).

The filler may include at least in part one or more fibers with mean diameters of between about 1 and 50 μm and it may at least in part include one or more fibers with mean diameters of between about 1 and 20 μm. Example fibers include RF 50/99 and RF 20/99 (Saint-Gobain™ K.K) and Nyglos 2 and Nyglos 4W (Nyco Minerals, Inc.). The filler may include at least in part a fiber containing $Al_2O_3$ and $SiO_2$ in about equal weight percentage amounts.

Substances may be added to promote adhesion or production of a sealed or hydrophobic surface, including substances that increase the pH of the mixture as noted above, including sodium hydroxide or potassium hydroxide, and hydrolyzable silanes that condense to form one or more cross-linked silicone-oxygen-silicon structures (siloxane bonds). Example materials are those that use one or more of the aforementioned colloidal silicates and clays, potassium hydroxide, and also use one or more substances that reduce the surface free energy of the surface. Such substances that reduce the surface free energy include halogenated compounds and fluoropolymer compounds, such as PTFE and PFA, including aqueous dispersions of such compounds, organofunctional hydrolyzable silanes, including those containing one or more fluorine atoms on one or more pendant carbon chains.

Among the substances that may be included in the coating material as one or more hydrolyzable silanes are components having the general formula $R_mSiX_n$ where R is alkyl chain and X is hydrolyzable, such a alkoxy group with m and n both integers and m+n=4. The hydrolyzable silane R may contain one or more halogen atoms. The hydrolyzable silane R may have a general formula of $CF_3(CF_2)_p(CH_2)_nSi$ (OCH$_2$CH$_3$)$_3$ where p is less than about 20 and may about 8 or less and where q is about 2. Other groups besides (OCH$_2$CH$_3$)$_3$, such as those based on methyl, propyl, or butyl groups, may be substituted and fall within the new art of this patent when they also are hydrolyzable. Other halogens, such as chlorine, may be substituted for the fluorine.

An example fluoroalkylalkoxysilane is tridecafluor-1,1,2, 2,-tetrahydrooctyltriethoxysilane. An example of such a silane is Dynasylan F8261 (Degussa Corp.).

The final coating produced may have a surface free energy (also referred to as the surface tension) of the coating is less than about 32 millinewtons/meter and may have a surface free energy less than about 25 millinewtons/meter and may have a surface free energy less than about 15 millinewtons/meter and may be less than about 10 millinewtons/meter.

The coating formulation may have materials added to modify its viscosity or surface tension. Examples of such materials are amorphous silica, such as in powder form. An example amorphous silica is fumed silica and precipitated silica. An example amorphous silica is CAB-O-SIL® HS-5 (Cabot Corporation). Surfactants may also be added to modify the viscosity or surface tension of the formulation.

The coating formulation may include amorphous silica mixed with a strong base. The amorphous silica-strong base mixture may be used to augment or replace some or all of a colloidal silicate material and be mixed with fillers or other materials such as hydrolyzable silanes.

FIG. 1 illustrates one embodiment of a method for preparing coating formulations in accordance with the present invention. As illustrated, the method of preparation may include the step of combining a combination of silica, an inorganic filler and a base in an amount sufficient to cause the combination to have a pH of at least 10.5 at some point during the preparation process, step 102. By way of example, the combining step 102 may comprise combining the constituents in varying orders and may include mixing, agitating and/or shaking the combination one or multiple times. In one approach, colloidal silica, at least one inorganic filler and potassium hydroxide may be combined. In another approach, an amorphous silica such as fumed silica, and potassium hydroxide may be initially combined, then colloidal silica and an inorganic filler may be added thereto. In yet another approach, the base may even be added later in the process (e.g., at step 106 or step 108, or between steps 106 and 108 noted below). In each approach, the base (e.g., potassium hydroxide) functions to effectively dissolve at least a portion of the silica. As further illustrated in FIG. 1, the method may optionally include the step of combining an alkoxy silane into the combination, step 106. As noted above, the additional of an alkoxy silane serves to enhance the non-stick properties of the coating formulation.

As illustrated in FIG. 1, the preparation method may further include the optional step of combining at least one of water, a surfactant and a solid into the combination, step 108. As previously noted, such constituents may be added to enhance the ability of the formulation to flow or otherwise cover surfaces to which the formulation may be applied. In relation to the optional steps, 106 and 108, the illustrated embodiment may also include the further step of waiting a predetermined time period after such step(s), step 110, so as to reduce the viscosity of the combination. In this regard, a waiting period after step 106 may serve to successively flocculate and peptize the silica. In relation to step 108, the waiting period may serve to allow for the hydrolization of silane alkoxy groups (e.g., when water is combined in step 108). As noted in FIG. 1, after step 102 and optional steps 106-110 have been completed, the prepared formulation may be utilized to coat an apparatus component such as a metal surface (e.g., an electrosurgical blade).

Figure 2:
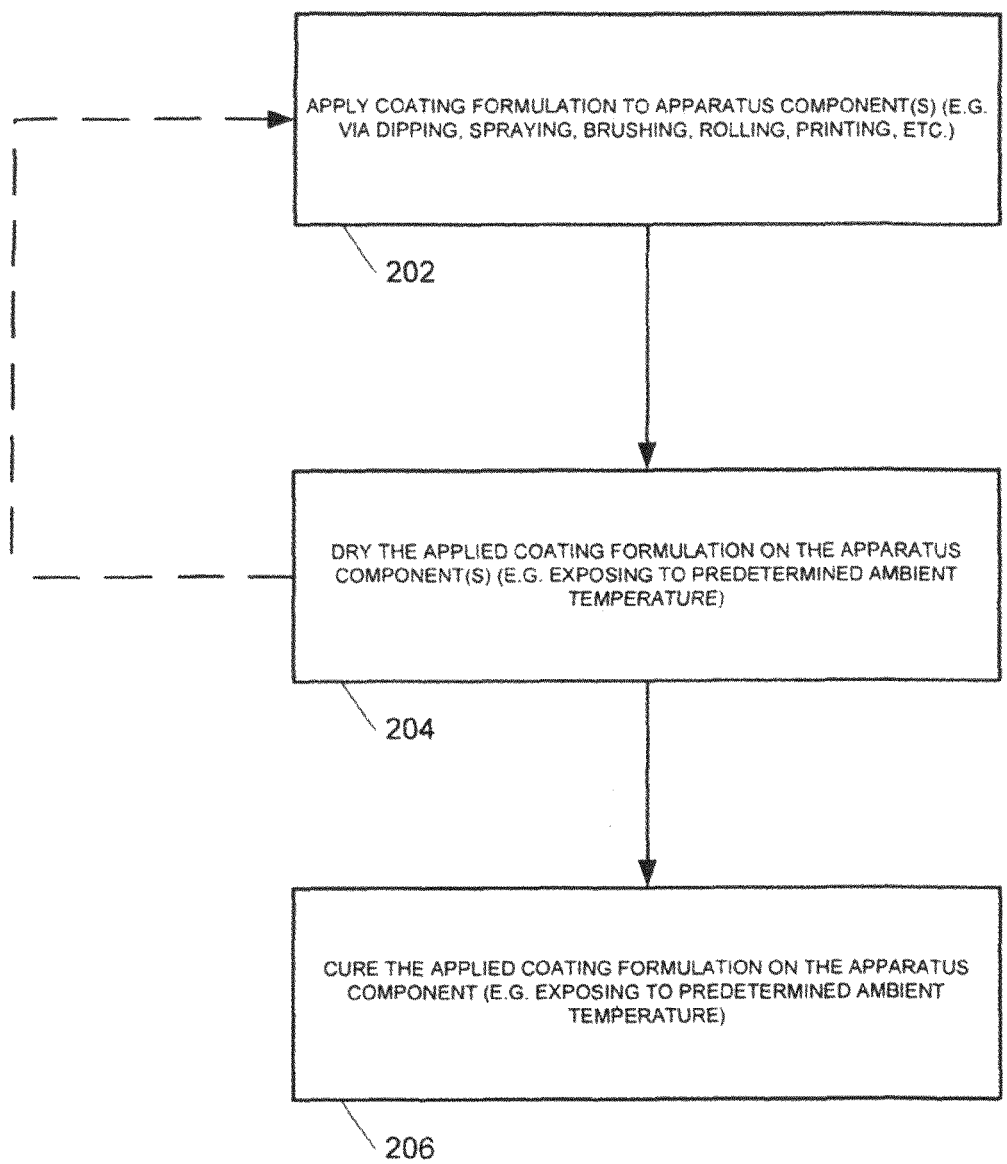
FIG. 2 illustrates one embodiment of a method of coating a surface of an apparatus coating with an inventive coating formulation prepared in accordance with the present invention.

In this regard, reference will now be made to FIG. 2 which illustrates an exemplary embodiment of a method of coating a surface of at least one apparatus component with the inventive formulations (e.g., a metal surface such as an electrosurgical blade). As shown, the method may include the steps of applying the coating formulation to the apparatus component surface, step 202, and drying the applied coating formulation on the apparatus component surface, step 204. The applying step 202 may be completed utilizing any of a variety of techniques, including for example, dipping, spraying, brushing, rolling, printing, etc. Similarly the drying step 204 may be completed in any manner that may function to remove liquid from the coating formulation so as to yield a dry coated apparatus component surface. By way of example, such drying step may include the sub-step of exposing the coated apparatus component to a predetermined temperature range sufficient to vaporize or otherwise remove liquid present in the formulation, and including an elevated ambient temperature for a predetermined time period. As noted, the coating step 202 and drying step 204 may be optionally repeated a number of times to desirably build-up the coating layer in increments and thereby enhance coverage and overall performance.

Following the drying step 204, the method may further include the step of curing the applied coating formulation on the apparatus component surface so as to yield a durable, high temperature surface coating, step 206. Further, depending upon the constituents used in the formulation, non-stick and other properties may be realized as otherwise described hereinabove. Of note, while separate drying and curing steps are shown in FIG. 2, it should be realized that an extended drying time period will also serve to cure the inventive formulations. As such, overlap may occur between the drying and curing stages of the process.

An example coating formulation, in weight percent, is

| | |
|---|---|
| Silica (from colloidal silica) | 20-30 |
| Filler | 15-30 |
| KOH | 8.5-10 |
| Water (from colloidal silica and KOH solution) | 35-50 |
| Fluorinated Silane | 0.25-5 |

A more specific example formulation is

| Component | Mass (gm) | % |
|---|---|---|
| Colloidal silica (Levasil 50/50) | 56.2 | 55.3 |
| Silica/Alumina fiber (RF 20/99) | 7.1 | 7.0 |
| Montmorillonite (Nanomer I.44P) | 16.5 | 16.2 |
| KOH (51 weight percent) | 18.8 | 18.5 |
| Fluorinated silane (F8261) | 2.3 | 2.3 |
| Fumed silica (HS-5) | 0.75 | 0.74 |

For example, the colloidal silica, filler, and KOH solution are combined and mixed by shaking for one minute. The fluorinated silane is then added and the mixture shaken 15 minutes. After shaking, wait 12 hours. During this period the mixture will become less viscous as the flocculated silica peptizes and the silane alkoxy groups hydrolyze. Add the fumed silica and shake five minutes. Wait one hour. The mixture may then be applied by dipping, spraying brushing, printing, or other means.

The coating may be applied using any means that conveys a liquid to the object to which the coating is to be applied.

Such methods include spraying, dipping, brushing, rolling, pad printing and printing. More than one coat may be applied, such as within 5 seconds and 4 hours of when previous coats were applied or within 5 seconds and 10 minutes of when previous coats were applied.

The coated article may be allowed to air dry at between about 60 and 200 degrees Fahrenheit for between about 1 and 8 hours and then cured at between about 350 and 500 degrees Fahrenheit for between about 15 minutes and one hour. The final cure temperature may be between about 400 to 475 degrees Fahrenheit. To reduce bubble formation during curing the temperature may be ramped between an air dry temperature and the final cure temperature such as, for example, over an interval of between about one and eight hours or over about three to six hours. The final cure may be immediately after air drying or it may be delayed.

A coated article may be a substantially organic surface such as cloth or wood to which the coating is applied and allowed to dry. For materials that cannot withstand high temperatures a cure temperature less than the temperature that damages the material may be used, such as 350 degrees, although longer cure times will be required than when higher temperatures are used.

A coated article may be a metal part, such as a component of an exhaust system, that needs to withstand temperatures exceeding, for example, 450 degrees Fahrenheit. The coated article may be a metal surface that benefits from having non-stick or reduced-stick properties, such as cookware or oven coatings. Such surfaces can be made from, for example, metal or glass. The coating may be applied to a glass surface to improve its non-stick properties. Articles may be coated to provide improved properties during elevated temperature service including temperatures over 450 degrees Fahrenheit. The coating may be applied articles expected to experience temperatures exceeding 600 degrees Fahrenheit, such as the surfaces near the edges of electrosurgical instruments where temperatures are believed to exceed 600 degrees Fahrenheit and may exceed 1,000 degrees Fahrenheit.

Figure 3:
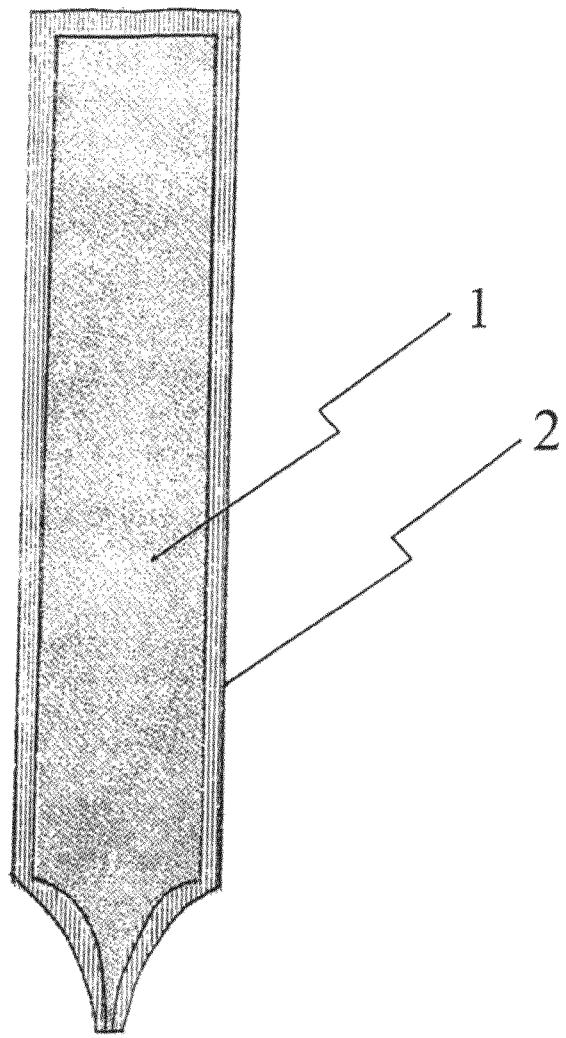
FIG. 3 portrays a cross section of a surgical blade with at least part of its surface insulated with a coating.

FIG. 3 illustrates the cross section of an electrosurgical instrument, in this case an electrosurgical blade, that has been at least partially coated. The preferred thickness of the coating using the formulation of the present invention is between about 0.001 and 0.1 inches and more preferably between about 0.002 and 0.010 inches. Preferably, at least part of the blade is left uncoated or with a coating that leads to an impedance less than about 5,000 ohms so that transfer of electrical energy is facilitated between the electrosurgical instrument and the tissue, such as when a very thin edge is exposed through the insulation. The blade body 1 is surrounded by insulation 2, defined by the inventive coating except for at least a portion of the peripheral edge. The length of the body extends into the page in this figure.

Various additional embodiments and modifications may be apparent to those skilled in the art and are within the scope of the present invention as defined by the claims which follow.

What is claimed is:

1. A process for providing an electrosurgical instrument in which a metal surface portion of an electrosurgical blade is coated at least in part with a coating formulation to provide an at least partially non-stick surface, comprising:
preparing a coating formulation by combining at least the following:
silica;
at least one inorganic filler;
at least one alkylalkoxysilane that includes at least one halogen; and,
a strong base in an amount so that the coating formulation has a pH of at least 10.5 during at least part of the preparing step;
waiting a predetermined time period after said preparing step; and,
coating at least a portion of said metal surface portion of the electrosurgical blade with said prepared coating formulation after said waiting step, wherein the coating step is completed so that a portion of the electrosurgical blade has an impedance from the electrosurgical blade to tissue of less than about 5,000 ohms, said portion comprising an edge of said electrosurgical blade exposed through the coating.

2. The process of claim 1, wherein said at least one halogen is comprised of at least one of:
chlorine; and
fluorine.

3. The process of claim 1, wherein said coating formulation has a pH of at least 12.5 during at least part of the preparing step.

4. The process of claim 1, wherein said preparing step further comprises:
combining water and a solid in said coating formulation.

5. The surgical instrument of claim 1, wherein said strong base is potassium hydroxide.

6. The process of claim 1, wherein said inorganic filler comprises montmorellonite.

7. The process of claim 1, further comprising:
waiting a predetermined time period after said preparing step and before said coating step.

8. The process of claim 1, wherein said coating step comprises:
applying the prepared coating formulation to said at least a portion of said at least one apparatus metal component surface; and,
drying the applied coating formulation on said at least one apparatus metal component surface to provide an at least partially non-stick surface.

9. The process of claim 8, further comprising:
repeating said applying step a plurality of times.

10. The process of claim 8, further comprising:
waiting a predetermined time period after said preparing step and before said coating step.

11. The process of claim 9, where said preparing step further comprises:
combining water in said coating formulation.

12. The process of claim 10, further comprising:
curing said applied coating formulation on said at least one apparatus metal component surface by applying thermal energy.

13. The process of claim 12, wherein said curing step is completed after said drying step.

14. The process of claim 1, wherein said coating step is completed so that at least part of the coating is between about 0.001 and 0.1 inches thick.

15. The process of claim 1, wherein said coating step is completed so that the coating has a surface free energy of less than about 32 millinewtons/meter.

16. The process of claim 1, wherein said electrosurgical blade comprises stainless steel.

17. The process of claim 1, wherein said at least one alkylalkoxysilane of said coating formulation is selected from a group consisting of:
fluoroalkylalkoxysilanes; and
chloroalkylalkoxysilanes.

18. The process of claim 17, wherein said fluoroalkylalkoxysilane is between 0.25 and 5 weight percent of said coating formulation.

* * * * *